United States Patent [19]

Dewanjee

[11] Patent Number: 4,553,974

[45] Date of Patent: Nov. 19, 1985

[54] TREATMENT OF COLLAGENOUS TISSUE WITH GLUTARALDEHYDE AND AMINODIPHOSPHONATE CALCIFICATION INHIBITOR

[75] Inventor: Mrinal K. Dewanjee, Rochester, N. Mex.

[73] Assignee: Mayo Foundation, Rochester, Minn.

[21] Appl. No.: 640,725

[22] Filed: Aug. 14, 1984

[51] Int. Cl.[4] .............................................. A63B 51/02
[52] U.S. Cl. ...................................... 8/94.11; 8/94.18; 8/94.33; 623/1; 623/2
[58] Field of Search .................... 8/94.11, 94.18, 94.33

[56] References Cited

U.S. PATENT DOCUMENTS

| | | | |
|---|---|---|---|
| 3,562,820 | 2/1971 | Braun | 8/94.11 |
| 3,962,433 | 6/1976 | Worms et al. | 424/212 |
| 3,966,401 | 6/1976 | Hancock et al. | 8/94.11 |
| 3,988,782 | 11/1976 | Dardik et al. | 8/94.11 |
| 4,098,571 | 7/1978 | Miyata et al. | 422/100 |
| 4,120,649 | 10/1978 | Schechter | 8/94.11 |
| 4,323,358 | 4/1982 | Lentz et al. | 8/94.11 |
| 4,378,224 | 3/1983 | Nimni et al. | 8/94.11 |
| 4,402,697 | 9/1983 | Pollock et al. | 8/94.11 |

OTHER PUBLICATIONS

M. Potokar, et al., Atherosclerosis, 30 (1978), 313-320.

Primary Examiner—A. Lionel Clingman
Attorney, Agent, or Firm—Charles J. Knuth; Peter C. Richardson; Mark Dryer

[57] ABSTRACT

A process for the treatment of collagenous tissue to adapt it for use in a prosthetic implant and to promote the growth of endothelial cells thereon after implantation comprising treatment with at least one surfactant prior to fixation, treatment with agents which inhibit calcification and agents which resist attack by phagocytic cells and optional treatment with stabilizing agents.

38 Claims, 7 Drawing Figures

TREATMENT OF COLLAGENOUS TISSUE WITH GLUTARALDEHYDE AND AMINODIPHOSPHONATE CALCIFICATION INHIBITOR

BACKGROUND OF THE INVENTION

This invention relates to a process for the treatment of collagenous tissue to render it suitable for use in prosthetic implants, and to the resulting tissue so treated. More particularly, the invention is concerned with a process for the treatment of collagenous tissue to adapt it to be used in a prosthetic implant and to promote the growth of endothelial cells thereon.

Prosthetic implants for use in humans have been known for some time and it also has been known to use natural tissue taken from animals including humans. When natural tissue is used in an implant it is necessary to treat it to avoid problems after implantation, for example excessive mineralization or calcification and rejection by the body's immune system. Numerous treatments for improving the stability of prosthetic devices made from natural tissue have been proposed in the prior art.

Thus U.S. Pat. No. 4,378,224 issued Mar. 29, 1983 to Nimni et al discloses a process for improving the biophysical stability of bioprostheses for heterograft or allograft implantation made from animal tissue involving the formation of cross-links in the protein structure of the tissue using the known cross-linking agent glutaraldehyde and soaking the tissue in an aqueous solution of a calcification inhibitor. Examples of suitable calcification inhibitors mentioned by Nimmi et al are diphosphonates and 3-amino-1-hydroxypropane 1,1-diphosphonic acid is mentioned as a typical diphosphonate, although no specific Example illustrating the use of this compound is given by Nimni et al.

Furthermore, although Nimni et al refer to harvesting and cleaning of the tissue prior to the glutaraldehyde treatment, there is no suggestion of any pre-treatment with an appropriate surfactant to remove, substantially completely, deleterious material present in the tissue. Accordingly, the coating (column 2 line 23) provided by Nimni et al is essentially a surface phenomenon and cross-linking with glutaraldehyde and stabilization with the calcification inhibitor throughout the fibrous matrix of the tissue is not and can not be achieved by the Nimni procedure.

U.S. Pat. No. 3,988,782 issued Nov. 2, 1976 to Dardik et al discloses the preparation of prostheses in the form of tubes, patches and conduits from arteries and veins of umbilical cords using glutaraldehyde as a hardening agent.

U.S. Pat. No. 3,966,401 issued June 29, 1976 to Hancock et al discloses the preparation of an implantable heart valve from porcine pericardial tissue in which the tissue is treated with glutaraldehyde as a tanning agent.

The inhibitory effect of various diphosphonates on aortic and kidney calcification in vivo is discussed in an article by M. Potokar and M. Schmidt-Dunker appearing in Atherosclerosis, 30 (1978) 313–320.

U.S. Pat. No. 4,120,649 issued Oct. 17, 1978 to Schechter discloses the treatment of transplants with glutaraldehyde to enhance the retention time in the recipient. As in Nimni et al, supra, the treatment is essentially a surface treatment and no additional stabilization or like treatment is disclosed.

U.S. Pat. No. 3,562,820 issued Feb. 21, 1971 to Braun, discloses the hardening with glutaraldehyde of tubular, strip and sheet form prostheses based on biological tissue.

U.S. Pat. No. 4,098,571 issued July 4, 1978 to Miyata et al discloses a process for preparing a heterograft substitute blood vessel which comprises treating a pig blood vessel with a proteolytic emzyme to digest unwanted material and retain collagenous and elastic fiber constituents and then fixing the resulting blood vessel with, inter alia, a mixture of formaldehyde and glutaraldehyde.

U.S. Pat. No. 4,323,358 issued Apr. 6, 1982 to Lentz et al discloses treatment of a glutaraldehyde-fixed animal tissue with a solution of a water-soluble salt of a sulfated higher aliphatic alcohol, such as sodium dodecyl sulfate, allegedly to inhibit calcification of the tissue after implantation.

Although all of the above prior art proposals have some degree of success, for example by inhibiting calcification to some extent and improving the biophysical stability of prosthetic implants to some extent, problems in these areas still remain. Furthermore, none of the aforesaid prior art disclosures express any recognition of the importance of promoting and enhancing the growth of endothelial cells on the surfaces of prosthetic implants.

The endothelium is a layer of flat cells lining various cavities within the body, in particular blood vessels. The lining of endothelial cells provides a smooth surface so that blood cells and platelets can flow without being damaged. Endothelial cells are capable of producing and secreting substances with a variety of actions and the actions occuring at the blood-endothelial interface contribute towards the well-being of the organism as a whole; for example, the intact endothelium is non-thrombogenic because both circulating blood cells and the endothelial surface have a negative charge and thus repel each other. Each endothelial cell is closely linked to its adjacent cells and the endothelial layer forms a selectively permeable membrane which resists the passive transfer of the fluid and cellular phases of blood.

While the intact endothelium acts as a primary barrier against the leakage of blood it also provides a prima facie indication to the body's immune system that foreign materials are not present, at least outside the blood vessels. However, if the endothelium is damaged, punctured or broken this automatically induces a response by the immune system which defends against foreign pathogens. The immune system, which is generally capable of discriminating between self and foreign antigens, operates through a complex assortment of lymphocytes and phagocytic cells whose activities are adapted to produce a coordinated protective response to foreign pathogens. Thus, among the phagocytic cells involved in the immune system, white blood cells or leukocytes function primarily to defend the body against microorganisms. Another important group of phagocytes is the macrophages which are widely distributed throughout the body and act in concert with other phagocytes associated with the linings of blood vessels, i.e. the endothelium, in, for example, the bone marrow, liver, spleen and lymph nodes.

A more detailed description of the immune system is not considered necessary for a full understanding of the present invention, but recognition of the role played by endothelial cells is important for an appreciation of the improvement provided by the invention over the prior art.

Surprisingly, it has now been found that by performing the process of the present invention and, in particular, ensuring substantially complete removal of deleterious material from collagenous material by the essential initial step of said process, the in vivo growth of endothelial cells upon prosthetic implants formed from tissue treated by the invention process is promoted. In addition to a marked improvement in the inhibition of mineralization or calcification upon implantation, this permits the formation of implants which are less susceptible to rejection by the body's immune system than any produced by prior art procedures.

SUMMARY OF THE INVENTION

In accordance with the invention there is provided a process for the treatment of collagenous tissue to adapt it for use in a prosthetic implant and to promote the growth of endothelial cells thereon after implantation, which comprises the steps of:

(a) contacting said tissue with at least one surfactant for a time sufficient to substantially completely remove deleterious material and open up the fibrous structure of the collagenous tissue;

(b) washing the resulting fibrous matrix to remove substantially are surfactant;

(c) fixing with glutaraldehyde; and (d) treating with a calcification-inhibiting agent, an agent which inhibits infiltration and attack by phagocytic cells upon implantation and/or an agent which inhibits infection; and, if desired, (e) treating the resulting agent/matrix tissue with a bond-stabilizing agent.

Collagen is a fibrous protein which occurs in vertebrates as the primary constituent of connective tissue fibrils. There are seven different types of collagen and type I is generally used for implants. Fibrous animal tissue normally contains collagen in association with other proteinaeous material, particularly elastin. As used herein the term collagenous tissue is intended to mean collagen tissue, particularly type I collagen, mixtures of collagen and elastin and animal tissues containing a significant proportion of collagen with or without elastin or other proteinaceous material. An essential requirement of the collagenous tissue to be used in the invention is that the protein molecules thereof contain free amino groups adapted to react with fixing or tanning reagents such as glutaraldehyde.

The preferred collagenous tissue is bovine pericardial tissue or porcine pericardial tissue. Such tissue is particularly suitable for the formation of the tissue leaflets in prosthetic heart valves, particularly those made in accordance with the teachings of Ionescu et al U.S. Pat. No. 4,388,735 issued June 21, 1983.

Other suitable forms of collagenous tissue which may be treated by the process of the invention are dura mater, fascia lata, valve tissue and vascular graft tissue.

Collagenous tissue, for example pericardial tissue, as it is initially removed from an animal requires cleaning to free it from unwanted contaminants. Usually the tissue is washed with sterile isotonic saline solution to remove excess blood and plasma proteins, and this conventional pre-washing is a desirable initial step before performing the essential step according to the process of the invention of contacting tissue with at least one surfactant for a time sufficient to substantially completely remove deleterious material.

As used herein the term deleterious material is intended to mean material which blocks or clogs the fibrous matrix of the collagen or collagen/elastin tissue to be used as a prosthetic implant, which material, if not removed, would provide sites to initiate an immune response in the host organism with consequential rejection of the implant or at least attack by host phagocytes. Deleterious material includes lipids, including lipoprotein and phospholipids, red blood cells, plasma protein, organelles and dead cell fragments, as well as free fatty acids, cholesterol, cholesterol esters and triglycerides.

The removal of deleterious material by the surfactant-treating step of the invention opens up the fibrous structure of the collagenous tissue and this enables the glutaraldehyde used in the subsequent fixing step to subtantially completely infiltrate the fibrous matrix of the collagenous tissue so that the reactive groups on the glutaraldehyde molecules bond to the free amino groups on the protein molecules of the collagenous tissue throughout the matrix.

Thus the surfactant treatment of the present invention serves the double purpose of, firstly, enabling the fibrous matrix of collagenous tissue to be thoroughly fixed throughout the matrix rather than merely on the surface; and, secondly, deleterious material is removed from the interstices of the fibrous matrix and is no longer present to be entrapped below the surface by the subsequent fixing step and to be available to present problems of rejection or attack by host phagocytes upon implantation. Prior art procedures which have advocated treatment with surfactants after the fixing step, for example U.S. Pat. No. 4,323,358 supra, are substantially ineffective for removing deleterious material which is effectively bonded to the tissue by the fixing agent.

It has been found that the particular sequence of steps according to the present invention provides a significant improvement in terms of implant retention over the prior art.

The surfactant used in the surfactant-treating step of the invention is a potent agent for removing deleterious material from animal tissue and care must be taken not to overdo the cleaning action and thereby damage the base tissue by using too strong a solution. On the other hand, the concentration of surfactant and the period of treatment must be sufficient to achieve the desired result of substantially completely removing the deleterious material. Within these criteria it is preferred to use the surfactant in the form of an aqueous solution containing 0.5 to 6% by weight of surfactant. A suitable treatment time is from two to six hours, preferably about three hours.

The surfactant may be an anionic surfactant, a non-ionic surfactant, an amphoteric surfactant or a mixture thereof.

Examples of suitable anionic surfactants are sodium dodecyl sulfate, sodium dodecyl sulfoacetate and sodium salt of alkaryl polyether sulfonate. Examples of suitable non-ionic surfactants are octylphenoxy polyethoxy ethanol (Triton X-100), polyoxyethylene (20) sorbitan monooleate (Tween 80), polyoxyethylene (20) sorbitan monostearate (Tween 60). Examples of suitable amphoteric surfactants are sulfobetaines commonly known as Zwittergents.

It has been found that particularly advantageous results are obtained if the surfactant is mixture of an anionic surfactant and a non-ionic surfactant; and a particularly preferred surfactant solution is one in which the anionic surfactant is 1% by weight sodium dodecyl sulfate and the non-ionic surfactant is 1% by weight octylphenoxy polyethoxy ethanol and/or 1% by weight polyoxyethylene (20) sorbitan monooleate. Preferably the collagenous tissue is contacted with said surfactant solution for about three hours at room temperature.

The surfactant is not only a potent cleansing agent but also a potential toxin and, accordingly, it is an important feature of the invention that, after the surfactant treatment, the fibrous matrix of collagenous tissue is thoroughly washed to remove substantially all surfactant. This washing step may be conducted in any conventional manner, for example with saline solution or distilled water, and, to ensure substantially complete removal of surfactant, the washing is continued until the formation of bubbles ceases.

After the above-described treatment with surfactant and the washing step to remove substantially all trace of surfactant the fibrous matrix of tissue resulting from the surfactant treatment is soaked in aqueous glutaraldehyde solution for a time sufficient to fix the tissue by bonding the glutaraldehyde molecules to substantially all the reactive amino groups present in the protein molecules of the tissue. A suitable time for the fixation step is from two to twelve hours and substantially complete fixation is achieved preferably by the repeated soaking procedure described hereinafter. Preferably, the concentration of glutaraldehyde is 0.25 to 1% by weight.

Fixation of animal tissue with glutaraldehyde to improve its characteristics and render it adaptable for prosthetic implants is known in the art and this step, in and of itself, is not claimed to be inventive. However, the special contribution provided by the invention with regard to this step is two-fold:

Firstly, the soaking with glutaraldehyde is carried out only after deleterious material has been substantially completely removed from the collagenous tissue by the surfactant treatment; thus ensuring that the fibrous matrix is adapted to be fixed throughout, rather than merely on its surfaces.

Secondly, substantially complete fixation throughout the fibrous matrix is ensured by soaking the tissue in the glutaraldehyde for a time sufficient to bond the reactive groups on the glutaraldehyde molecules to substantially all the reactive amino groups present in the protein molecules of the tissue.

The described result is preferably achieved by repeated soakings in glutaraldehyde to effect multiple cross-linking in accordance with the procedure described hereinafter. The need for repeated soakings, not only in glutaraldehyde to effect multiple cross-linking, but also in calcification-inhibiting agents and anti-phagocytic agents, as described hereinafter, to achieve the cumulative saturation effect provided by the process of this invention has not been achieved in the prior art.

According to a preferred embodiment of the invention the tissue is soaked in 0.5% by weight glutaraldehyde solution in the presence of 0.1M acetate buffer for a period of about three and a half hours. Subsequently, excess glutaraldehyde is washed from the tissue.

An important aspect of the invention is the inhibition of calcification on prosthetic implants formed from tissue treated in accordance with the process of the invention.

It has been found that the presence of phosphate ions tends to increase the occurrence of calcification and accordingly the use of phosphate buffers in the steps of the inventive process is to be avoided, notwithstanding the efficiency of the intermediate washing steps.

Since control of pH is an important feature during the process, such control preferably is achieved with a non-phosphate buffer, preferably an acetate buffer.

The tissue fixed with glutaraldehyde is further treated in accordance with the invention firstly with a calcification-inhibiting agent and/or an agent which inhibits infiltration and attack by phagocytic cells upon implantation and finally with an agent, usually a reducing agent, which stabilizes the molecular bonds of the resulting agent/matrix tissue.

Mineralization, or more particularly calcification, on and around tissue implants after implantation results in reduced flexibility of the tissue and therefore decreased efficiency in the operation of the prosthesis in the host body. Various treatments have been proposed in the prior art to inhibit or reduce calcification and these have met with some degree of success. In particular, the use of specific compounds to inhibit calcification is known in the art. However, the special application of known calcification inhibitors, especially amino diphosphonates, in accordance with the process of the present invention results in a substantial improvement over prior art treatments and unexpected advantages in areas not investigated in prior art procedures.

Thus, prosthetic implants made from collagenous tissue treated in accordance with the process of the present invention are found to be effective in resisting not only calcification but also thrombosis, infection and degeneration. These advantageous characteristics, which are exhibited to a degree substantially greater than that achieved in the prior art, are attributable to the fact that endothelial cell coverage on the implant is encouraged and the promotion of such coverage protects the implant from the reactions leading to thrombosis, calcification, infection and degeneration.

The stated improvement is attained by the particular combination of steps described above in which the agent used in the further treatment of the fixed tissue, as well as a calcification agent, may be an agent which inhibits infiltration and attack by phagocytic cells, for example, a sporin antibiotic having a free reactive amino group or methotrexate; or an agent which inhibits infection, preferably cephalosporin C.

The said sporin antibiotic is derived from cyclosporin A, a known immunosuppresive drug having a molecular weight of 1202 and the structural formula illustrated in FIG. 7 of the accompanying drawings.

For use as a treating agent in the process of the present invention the cyclopsorin A ring is opened at the position indicated by the arrow in the formula, to provide a free amino group for reaction with the free reactive groups on the glutaraldehyde molecules attached to the fixed tissue.

Methotrexate, or N-[4-[[(2,4-diamino-6-pteridinyl)-methyl]methylamino]benzoyl]-L-glutamic acid is a known folic acid antagonist and antimetabolite having the formula:

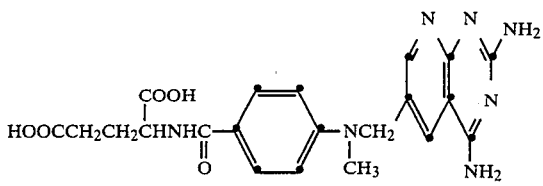

This drug has two free amino groups available for reaction with the reactive groups on the glutaraldehyde-fixed tissue matrix.

Cephalosporin C is a known potent inhibitor of infection.

For convenience in terminology, the calcification inhibiting agents and the immuno-suppressive agents and drugs used in the post-fixing step of the process according to the invention are referred to hereinafter by the generic term "drug" and, under this terminology, the desired effect produced by the process may be termed "drug immobilization" or "immunosuppression".

One of the advantageous results achieved by the drug immobilization provided by the process of the invention is an effective balance between:

(1) the encouragement or promotion of endothelial cell coverage;

(2) the enhancement of would healing; and (3) inhibition of rejection and attack by macrophage and other phagocytes.

A preferred application for tissue subjected to drug immobilization by the process of the invention is in the production of prosthetic heart valves wherein the leaflets and sewing ring are formed from the treated tissue. A particularly preferred embodiment of the tissue is produced when the drug is an amino diphosphonate calcium inhibitor and it has been found that prosthetic heart valves made from the preferred embodiment conform to the above balance in that examination of the prosthesis some two months after implantation shows:

(1) Substantially complete endothelial cell coverage over the leaflets and sewing ring and no evidence of thrombosis, calcification, infection or degeneration;

(2) Substantially complete would healing with no evidence of macrophage debris or macrophage factor; and (3) No evidence of rejection or inhibition of endothelial cell growth by microphage (monocyte) attack.

The drug immobilization process preferably is completed by stabilizing the fixed and drug-treated tissue with a reducing agent. Although in theory any reducing agent which will effectively reduce double bonds between carbon and nitrogen atoms may be used for this step including cyanoborohydride; to avoid any possible problems from toxic residues, the preferred reducing agent is sodium borohydride (NaBH$_4$).

Thus, the preferred embodiment of the invention provides a process for the treatment of collagenous tissue to adapt it for use in a prosthetic implant and to promote the growth of endothelial cells thereon after implantation which comprises the sequential combination of the following steps:

(1) contacting the tissue with at least one surfactant for a time sufficient to substantially completely remove deleterious material and open up the fibrous structure to form a matrix substantially free from lipids, red blood cells, plasma protein, organelles, and dead cell fragments;

(2) rinsing the cleaned fibrous matrix resulting from step 1 with distilled water or saline solution to remove substantially all surfactant;

(3) soaking said matrix in aqueous glutaraldehyde solution for a time sufficient to bond the glutaraldehyde molecules to substantially all the reactive amino groups present in the protein molecules of the tissue;

(4) washing the glutaraldehyde-fixed tissue to remove excess glutaraldehyde;

(5) treating the fixed tissue with an aqueous solution of amino diphosphonate for a time sufficient to bond substantially all the free reactive groups of the bonded glutaraldehyde molecules to the reactive amino groups of the amino diphosphonate;

(6) washing to remove excess amino diphosphonate; and, if desired, (7) treating the diphosphonate-bonded tissue matrix with sodium borohydride to stabilize the bonding of the amino diphosphonate and glutaraldehyde to the protein molecules of the tissue;

(8) washing to remove excess sodium borohydride and, if desired, storing the resulting treated tissue in aqueous formaldehyde for subsequent use.

The preferred collagenous tissue is bovine or porcine pericardial tissue. Alternatively, the collagenous tissue may be dura meta, fascia lata, falve tissue or vascular graft tissue.

Preferably, the collagenous tissue is pre-washed with isotonic saline solution to remove excess blood and plasma proteins prior to treatment with surfactant in step (1).

Preferably, step (1) is carried out with an aqueous solution containing 0.5 to 6% by weight of surfactant; the surfactant preferably being selected from those listed above. Particularly desirable results are obtained when said surfactant is a mixture of an anionic surfactant and a non-ionic surfactant.

A particularly preferred surfactant solution is one in which the anionic surfactant is 1% by weight sodium dodecyl sulfate and the non-ionic surfactant is 1% by weight octylphenoxy polyethoxy ethanol and/or 1% by weight polyoxyethylene (20) sorbitan monooleate.

In carrying out step (1) it has been found that the sufficient time requirement is fulfilled when the collagenous tissue is contacted with said surfactant solution for two to six hours, preferably about three hours, at room temperature.

The fixing treatment of step (3) preferably is conducted in a solution having a glutaraldehyde concentration of 0.25 to 1% by weight.

As described above, when treating collagenous tissue, particularly pericardial tissue, with a fixing solution this step is conducted by soaking the collagenous tissue in 0.5% by weight glutaraldehyde in the presence of 0.1M acetate buffer for a period of about three and a half hours.

The glutaraldehyde-fixed tissue is then carefully washed, for example with deionized or acetate-buffered water, to remove excess glutaraldehyde and then treated according to step (5).

Preferably, the amino diphosphonate used in step (5) is selected from compounds of the formula:

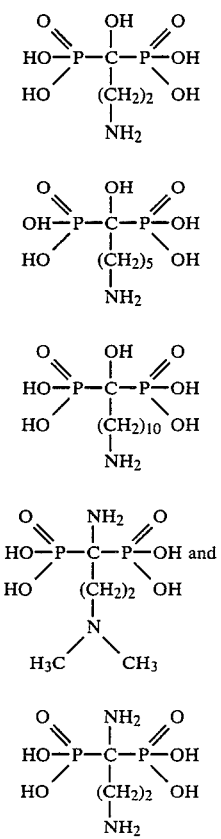

(1)
(2)
(3)
(4)
(5)

A particularly preferred amino diphosphonate is 3-amino-1-hydroxypropane-1,1-diphosphonic acid of formula (1) and preferably the tissue is soaked in fresh saturated solutions of said amino diphosphonate in distilled water (16 mg/ml.) at a pH of 8.0 for three hours per day in each fresh solution over a period of three days.

Particularly advantageous results are obtained if the tissue is soaked in glutaraldehyde between each fresh soaking in amino diphosphonate. This in effect means repetition of steps (3), (4) and (5).

The cumulative effect of multiple cross-linking on drug uptake (i.e. amino diphosphonate uptake) by following this procedure is illustrated graphically in FIG. 3 of the accompanying drawings; and this effect, as well as the effect of surfactant, temperature and fixation time on drug uptake is discussed hereinafter.

The next preferred step in the treatment of the tissue after drug uptake is stabilization with sodium borohydride and this step (7) preferably is conducted with a solution having a concentration of sodium borohydride of 5 to 10 mg/ml.

The process of the preferred embodiment is summarized in the following reaction scheme, wherein protein —NH$_2$ represent a molecule of collagen or elastin in the collagenous tissue containing one free amino group and DP-NH$_2$ represent a molecule of amino diphosphonate containing one free amino group.

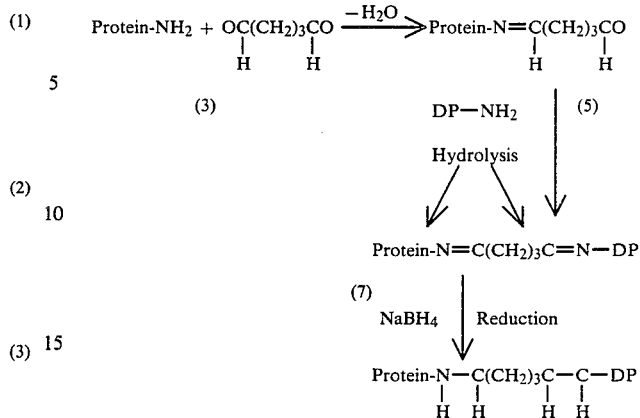

In the above reaction scheme the numerals (3), (5) and (7) identify the relevant steps of the process and the final formula illustrates a fully saturated conjugate containing a terminal diphosphonate group.

BRIEF DESCRIPTION OF THE DRAWINGS

The present invention will be more particularly described by reference to the accompanying drawings in which.

In the graphs of FIGS. 1 to 5, the term "drug" means 3-amino-1-hydroxypropane-1, 1-diphosphonic acid. Comparable results are obtainable with other amino diphosphonates in accordance with the invention.

The following Example illustrates in more detail the preferred embodiment of the invention.

EXAMPLE

The pericardium was removed from the heart of a calf. The pericardial tissue was then washed with 0.9% saline solution to remove excess blood and plasma proteins.

Fatty tissue and thick adherent tissue were removed.

The cleaned fat-free pericardial tissue was then cut into (5–10 cm × 5–10 cm) pieces and each piece of tissue (hereinafter referred to simply as "tissue") was treated according to the following procedure.

The tissue was immersed in a surfactant solution comprising 1% by weight sodium dodecyl sulfate and 1% by weight octylphenoxy polyethoxy ethanol, commercially available under the Trade Mark Triton X-100. The tissue was soaked in the surfactant solution at room temperature (23° to 25° C.) for a period of three hours.

The tissue was removed from the surfactant solution and thoroughly rinsed with saline solution in a strainer until no more bubbles were seen coming from the tissue and vesicles were removed by suction and washings. It is to be understood that the importance of this washing step is to ensure substantially complete removal of surfactant from the tissue and the nature of the washing solution is not critical, for example, distilled water, deionized water or 0.05M acetate buffer solution having a pH of 5.5 may be used instead of saline solution.

After the aforesaid washing step, the tissue was soaked in 0.5% by weight glutaraldehyde in 0.1M acetate buffer solution for about three and a half hours.

The fixed tissue was rinsed in 0.05M acetate buffer (or deionized water) to remove excess glutaraldehyde and immersed in a saturated drug solution comprising 16 mg/ml. of 3-amino-1-hydroxypropane-1,1-diphosphonic acid in 0.05M acetate buffer. The tissue was soaked in the drug solution for a period of two to three hours.

After the initial drug bonding step the tissue was reimmersed in 0.05M acetate buffer/glutaraldehyde solution and soaked therein for twelve hours.

The tissue was then again rinsed and soaked in drug solution for a period of two to three hours.

The fixation and drug-bonding steps were then repeated two more times.

Figure 3:
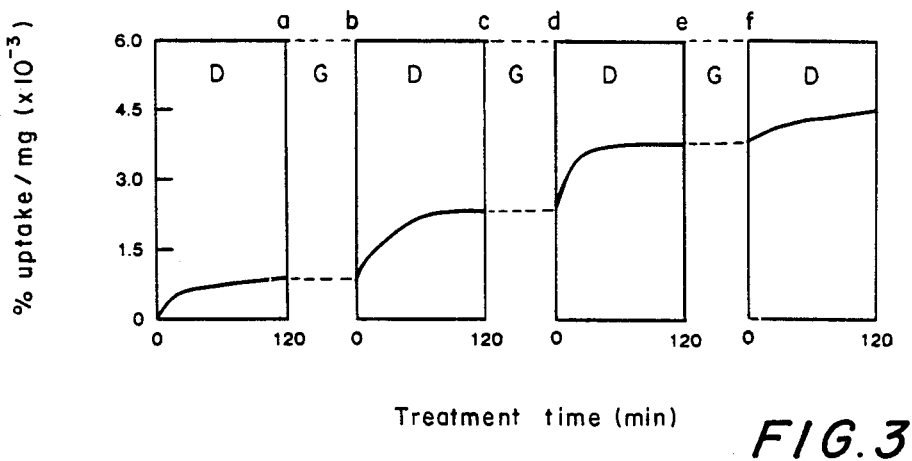
FIG. 3 is a graph illustrating the effect of multiple cross-linking (fixation) on drug uptake.

The cumulative effect of repeating the glutaraldehyde and amino diphosphonate treatments is illustrated graphically in FIG. 3 of the accompanying drawings and these steps may be repeated as long as there is any significant increase in drug uptake. In practice, the performance of each step four times, i.e. three repetitions of each, is normally sufficient to obtain substantially maximum uptake of drug. The overall process is dependent upon the amino group conjugation of amino diphosphonate via glutaraldehyde to the amino acid (lysine) of the collagen or elastin in the tissue.

After the final repetition of the drug treatment the tissue was soaked in a solution containing 5 mg/ml of sodium borohydride for thirty minutes at 25° C.

Finally the tissue was removed from the sodium borohydride solution, rinsed to remove excess borohydride and placed in storage under 0.5% glutaraldehyde or formaldehyde solution until required for use.

Tissue valves prepared from tissue treated according to the above procedure are normally kept in 4% formaldehyde solution until required for implantation.

It is important to note that, before implantation, the valve may be rinsed with sodium borohydride solution or glycine (10 mg/ml) to remove formaldehyde. The removal of formaldehyde reduces tissue necrosis and enhances wound healing.

Figure 6:
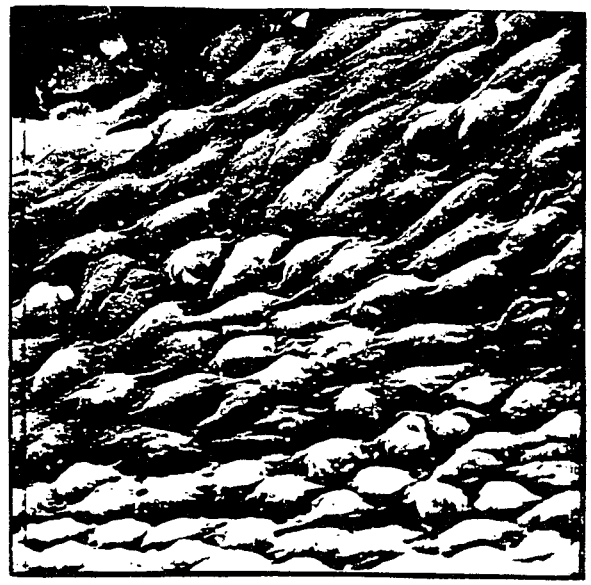
FIG. 6 is a scanning electron micrograph, magnification X2000, showing endothelial cell coverage on a valve made from pericardial tissue treated in accordance with the invention after two months in a calf.
Figure 7:
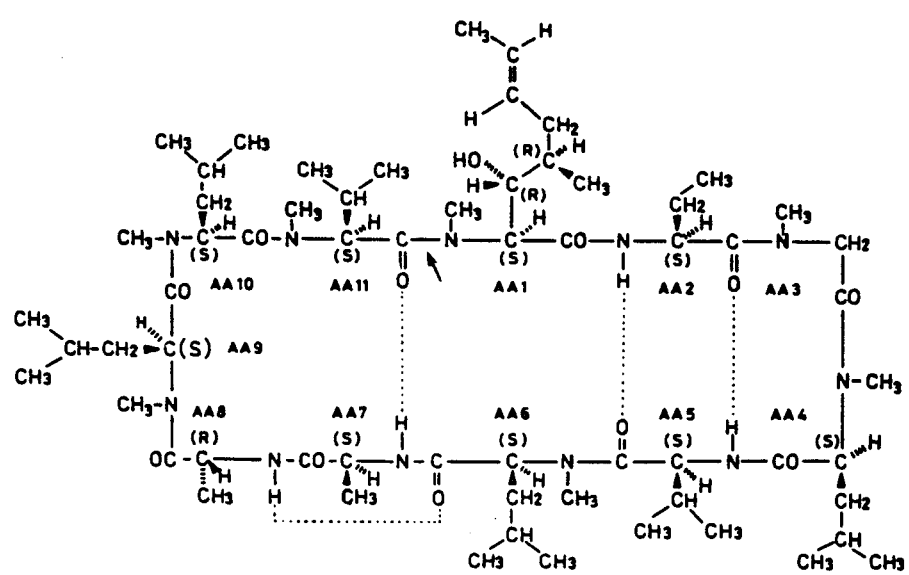
FIG. 7 illustrates the structural formula of cyclosporin A.

A number of tissue valves were made from tissue treated in accordance with the procedure illustrated in the above Example and these valves were implanted in calves. The calves were slaughtered after two months and the valves examined. There were no signs of calcification and endothelial cell coverage was substantial as indicated in FIG. 6 of the accompanying drawings. These results demonstrate the substantial improvement achieved by the process of the present invention.

The improved effects achieved by the process of the present invention are demonstrated by the results illustrated graphically in FIGS. 1 to 5 of the drawings and shown photographically in FIG. 6 of the drawings.

Figure 1:
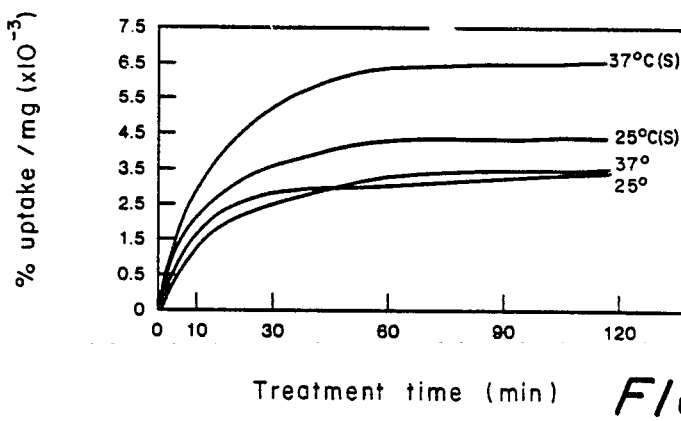
FIG. 1 is a graph illustrating the effect of temperature and surfactant on drug uptake.

Referring to FIG. 1 of the drawings, it will be seen that uptake of drug increases steadily for about 30 minutes at room temperature (25° C.) reaching a maximum of about 2.9% without a surfactant pretreatment. Further soaking time and increase of temperature, up to 37° C., has very little effect on the drug uptake.

Treatment of the tissue with surfactant according to the process of the invention, indicated by curves (S), not only increases the uptake time, up to 60 minutes, but also increases the amount of drug taken up by the tissue. Furthermore, the drug uptake is more temperature dependent and treatment at 37° C. increases the drug uptake by 2% over that achieved at 25° C.

Figure 2:
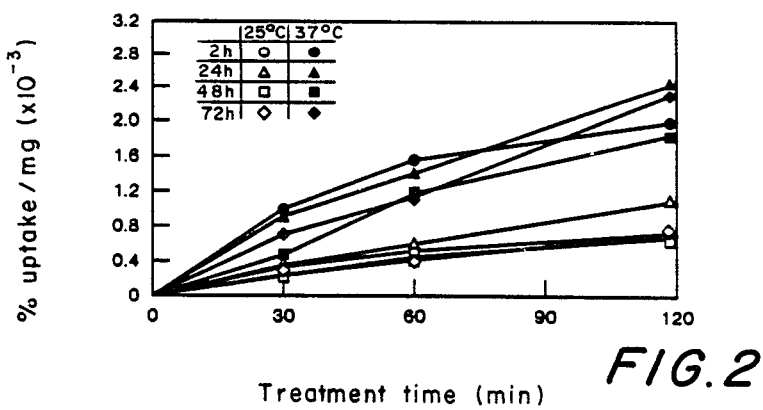
FIG. 2 is a graph illustrating the effect of fixation time and temperature on drug uptake.

FIG. 2 illustrates the effect of fixation time and temperature on drug uptake. It is to be noted that increased fixation time does not necessarily increase the drug uptake. A fixation time of 24 hours appears to be optimum for maximum drug uptake up to a drug treatment time of two hours. However, increasing the temperature of fixation, from 25° C. to 37° C., provides a significant increase in drug uptake.

FIG. 3 illustrates the effect of multiple cross-linking, i.e. repeated fixation treatments, on drug uptake. Starting at time 0 with a tissue initially fixed in glutaraldehyde according to the procedure described hereinabove, this graph illustrates the effect of repeated drug treatments, D, of periods of 120 minutes each intersperced with repeated treatments with glutaraldehyde, G, represented by the arbitrary time periods ab, cd and ef. These fixation periods may vary from two or three up to about twelve hours, indicated by broken lines in the drawing, and naturally there is no drug uptake during these fixation periods. However, by following this repetitive procedure the effect is cumulative and a considerable increase in drug intake is achieved. It will be noted that the curve for the drug uptake at the end of the first treatment period has almost flattened out and the subsequent increases achieved by following the stated repetitive procedure is totally unexpected and certainly not attained or attainable by the procedures disclosed in the prior art.

Figure 4:
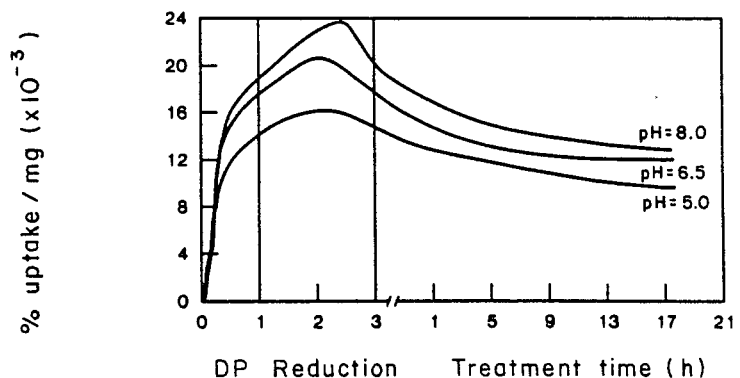
FIG. 4 is a graph illustrating the effect of pH on drug bonding.

FIG. 4 illustrates the effect of pH on drug (DP) bonding followed by reduction with sodium borohydride. It will be seen that bonding trends to increase with more alkaline solutions.

Figure 5:
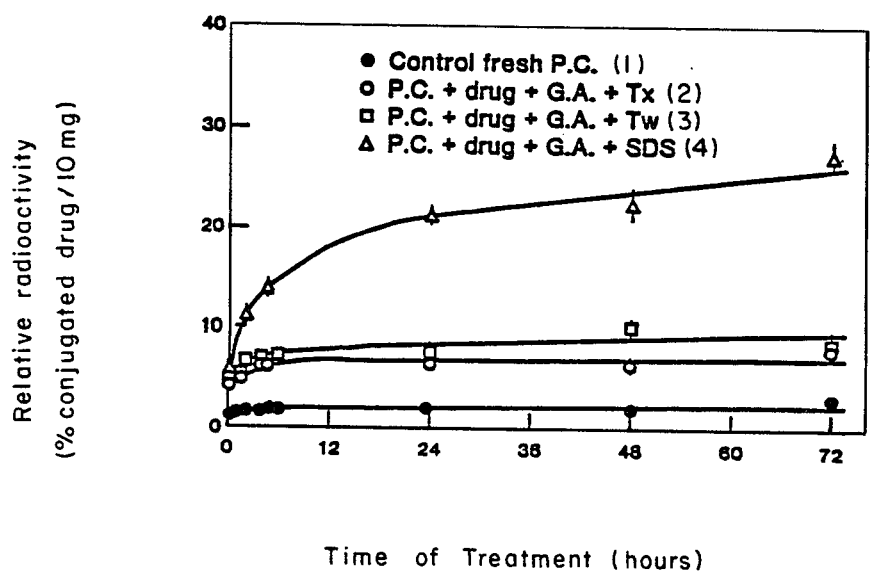
FIG. 5 is a graph illustrating the enhanced drug binding to pericardium achieved following the initial treatment with surfactant.

The effect of the initial surfactant treatment in enhancing the binding of the drug to pericardial tissue is illustrated in FIG. 5. The percentage of drug conjugated to the tissue was determined by use of radioactive tracers and the tests were conducted to compare the drug uptake achieved using (1) fresh pericardial tissue with no surfactant or fixation as a control; (2) pericardial tissue fixed with glutaraldehyde (G.A.) after treatment with Triton X-100 (Tx); (3) pericardial tissue fixed with glutaraldehyde after treatment with polyoxyethylene (20) sorbitan monooleate, commercially available under the Trade Mark Tween (Tw); and (4) paricardial tissue fixed with glutaraldehyde after treatment with sodium dodecyl sulfate (SDS).

It will be seen that an significant increase in drug uptake is achieved following the pre-treatment with sodium dodecyl sulfate, an anionic surfactant. This effect is even further enhanced by using a mixture of anionic and non-ionic surfactants according to the preferred embodiment of the invention.

FIG. 6 shows the substantially complete coverage of the tissue surface with endothelial cells achieved after an implantation time of only two months. This effect serves to demonstrate the success of the implant and, in particular, the achievement of the advantageous results

I claim:

1. A process for the treatment of collagenous tissue to adapt it for use in a prosthetic implant and to promote the growth of endothelial cells thereon after implantation, which comprises the steps of:
   (a) contacting said tissue with at least one surfactant for a time sufficient to substantially completely remove deleterious material and open up the fibrous structure of the collagenous tissue;
   (b) washing the resulting fibrous matrix to remove substantially all surfactant;
   (c) fixing the washed tissue with glutaraldehyde;
   (d) treating the glutaraldehyde-fixed tissue with a calcification-inhibiting agent, an agent which inhibits infiltration and attack by phagocytic cells upon implantation and/or an agent which inhibits infection; and
   (e) treating the resulting agent/matrix tissue with a reducing agent to stabilize the bonding of the glutaraldehyde of step (c) and the agent of step (d) to the tissue.

2. A process according to claim 1, in which the collagenous tissue is bovine or porcine pericardial tissue.

3. A process according to claim 1, in which the collagenous tissue is dura mater, fascia lata, valve tissue or vascular graft tissue.

4. A process according to claim 1, in which the surfactant is in the form of an aqueous solution containing 0.5 to 6% by weight of surfactant.

5. A process according to claim 4, in which said surfactant is a mixture of an anionic surfactant and a non-ionic surfactant.

6. A process according to claim 5, in which the anionic surfactant is 1% by weight sodium dodecyl sulfate and the non-ionic surfactant is 1% by weight octylphenoxy polyethoxy ethanol and/or 1% by weight polyoxyethylene (20) sorbitan monooleate.

7. A process according to claim 6, in which the collagenous tissue is contacted with said surfactant solution for about three hours at room temperature.

8. A process according to claim 4, in which the surfactant is an amphoteric surfactant.

9. A process according to claim 1, in which the collagenous tissue is pre-washed with saline solution to remove excess blood and plasma proteins, prior to treatment with surfactant.

10. A process according to claim 1, in which the fibrous matrix of tissue resulting from the surfactant treatment is soaked in aqueous glutaraldehyde solution for a time sufficient to fix the tissue by bonding the glutaraldehyde molecules to substantially all the reactive amino groups present in the protein molecules of the tissue.

11. A process according to claim 10, in which the concentration of glutaraldehyde is 0.25 to 1% by weight.

12. A process according to claim 11, in which the tissue is soaked in 0.5% by weight glutaraldehyde solution in the presence of 0.1M acetate buffer for a period of about three and a half hours, after which excess glutaraldehyde is washed from the tissue.

13. A process according to claim 10, in which the glutaraldehyde-fixed tissue is treated with a calcification-inhibiting agent containing reactive amino groups for a time sufficient to bond substantially all the free reactive groups of the bonded glutaraldehyde molecules to the reactive amino groups of the calcification-inhibiting agent.

14. The process according to claim 13, in which the calcification-inhibiting agent is an amino diphosphonate.

15. A process according to claim 14, in which the amino diphosphonate is selected from compounds of the formula:

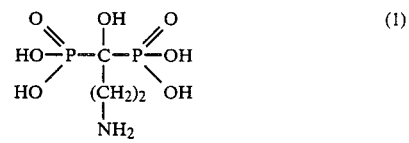

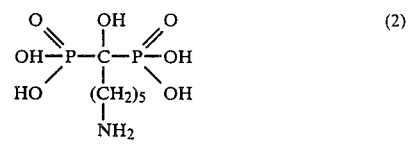

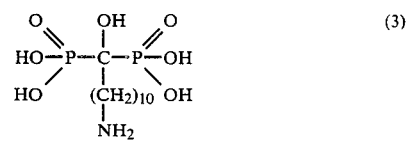

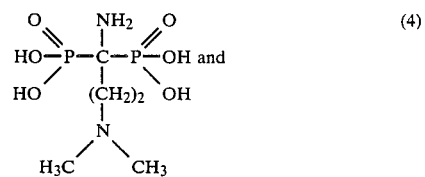

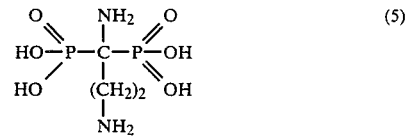

16. A process according to claim 15, in which the amino diphosphonate is 3-amino-1-hydroxypropane-1,1-diphosphonic acid of formula (1) and the tissue is soaked in fresh saturated solutions of said amino diphosphonate in distilled water at a pH of 8.0 for three hours per day in each fresh solution over a period of three days.

17. A process according to claim 16, in which the tissue is soaked in glutaraldehyde between each fresh soaking with amino diphosphonate.

18. A process according to claim 14, in which the tissue is further treated with 5 to 10 mg/ml of sodium borohydride to stabilize the bonding of the amino diphosphonate and glutaraldehyde to the protein molecules of the tissue.

19. A process according to claim 10, in which the glutaraldehyde-fixed tissue is treated with (i) an agent which inhibits infiltration and attack by phagocytic cells or (ii) an agent which inhibits infection.

20. A process according to claim 19, in which said agent (i) is a sporin antibiotic having a free reactive amino group or methotrexate and said agent (ii) is cephalosporin C.

21. A process according to claim 19, in which the tissue is treated with sodium borohydride to stabilize the bonding of agent (i) or agent (ii) to the treated tissue.

22. A process for the treatment of collagenous tissue to adapt it for use in a prosthetic implant and to promote the growth of endothelial cells thereon after implantation which comprises the sequential combination of the following steps:
(1) contacting the tissue with at least one surfactant for a time sufficient to substantially completely remove deleterious material and open up the fibrous structure to form a matrix substantially free from lipids, red blood cells, plasma protein, organelles, and dead cell fragments;
(2) rinsing the cleaned fibrous matrix resulting from step 1 with distilled water or saline solution to remove substantially all surfactant;
(3) soaking said matrix in aqueous glutaraldehyde solution for a time sufficient to bond the glutaraldehyde molecules to substantially all the reactive amino groups present in the protein molecules of the tissue;
(4) washing the glutaraldehyde-fixed tissue to remove excess glutaraldehyde;
(5) treating the fixed tissue with an aqueous solution of amino diphosphonate containing reactive amino groups for a time sufficient to bond substantially all the free reactive groups of the bonded glutaraldehyde molecules to the reactive amino groups of the amino diphosphonate;
(6) washing to remove excess amino diphosphonate; and
(7) treating the diphosphonate-bonded tissue matrix with sodium borohydride to stabilize the bonding of the amino diphosphonate and glutaraldehyde to the protein molecules of the tissue; and
(8) washing to remove excess sodium borohydride and, if desired, storing the resulting treated tissue in aqueous formaldehyde for subsequent use.

23. A process according to claim 22, in which the collogenous tissue is bovine or porcine pericardial tissue.

24. A process according to claim 22, in which the collagenous tissue is dura mater, fascia lata, valve tissue or vascular graft tissue.

25. A process according to claim 22, in which said collagenous tissue is pre-washed with isotonic saline solution to remove excess blood and plasma proteins prior to treatment with surfactant in step (1).

26. A process according to claim 22, in which step (1) is carried out with an aqueous solution containing 0.5 to 6% by weight of surfactant.

27. A process according to claim 26, in which said surfactant is a mixture of an anionic surfactant and a non-ionic surfactant.

28. A process according to claim 27, in which the anionic surfactant is 1% by weight sodium dodecyl sulfate and the non-ionic surfactant is 1% by weight octylphenoxy polyethoxy ethanol and/or 1% by weight polyoxyethylene (20) sorbitan monooleate.

29. A process according to claim 28, in which the collagenous tissue is contacted with said surfactant solution for three hours at room temperature.

30. A process according to claim 26, in which the surfactant is an amphoteric surfactant.

31. A process according to claim 22, in which step (3) is conducted in a solution having a glutaraldehyde concentration of 0.25 to 1% by weight.

32. A process according to claim 22, in which step (3) is conducted by soaking the collagenous tissue in 0.5% by weight glutaraldehyde in the presence of 0.1M acetate buffer for a period of about three and a half hours.

33. A process according to claim 22, in which the amino diphosphonate used in step (5) is selected from compounds of the formula:

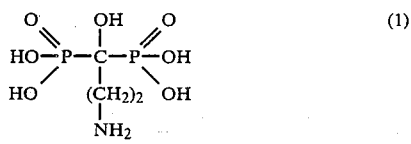
(1)

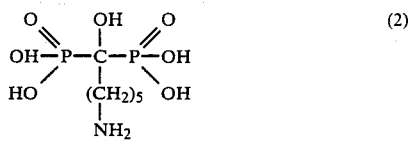
(2)

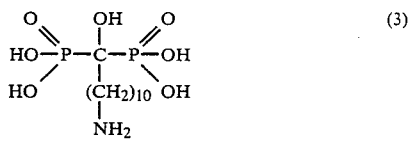
(3)

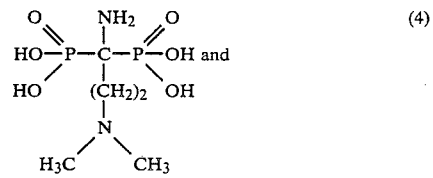
(4)

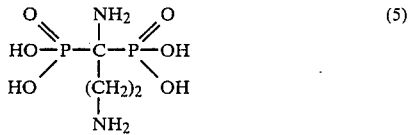
(5)

34. A process according to claim 32, in which the amino diphosphonate is 3-amino-1-hydroxypropane-1,1-diphosphonic acid of formula (1) and the tissue is soaked in fresh saturated solutions of said amino diphosphonate in distilled water at a pH of 8.0 for three hours per day in each fresh solution over a period of three days.

35. A process according to claim 34, in which the tissue is soaked with glutaraldehyde between each fresh soaking with amino diphosphonate.

36. A process according to claim 22, in which step (7) is conducted with a solution having a concentration of sodium borohydride of 5 to 10 mg/ml.

37. A fixed and stabilized collagenous tissue adapted for use in a prosthetic implant produced by a process according to claim 22.

38. A storage-stable pack comprising a tissue according to claim 37 immersed in aqueous formaldehyde solution.

* * * * *